United States Patent
Chuang et al.

(10) Patent No.: US 9,315,815 B2
(45) Date of Patent: Apr. 19, 2016

(54) METHOD OF HIGH-THROUGHPUT SORTING OF HIGH EXPRESSION CELL AND CELLS SORTED THEREFROM

(71) Applicant: Taipei Medical University, Taipei (TW)

(72) Inventors: Kuo-Hsiang Chuang, Taipei (TW); Tian-Lu Cheng, Taipei (TW); I-Shiuan Chiang, Taipei (TW); Yuan-Chin Hsieh, Taipei (TW)

(73) Assignee: Taipei Medical University, Taipei (TW)

( * ) Notice: Subject to any disclaimer, the term of this patent is extended or adjusted under 35 U.S.C. 154(b) by 86 days.

(21) Appl. No.: 14/263,759

(22) Filed: Apr. 28, 2014

(65) Prior Publication Data

US 2015/0118693 A1 Apr. 30, 2015

(30) Foreign Application Priority Data

Oct. 29, 2013 (TW) .............................. 102139138 A (51) Int. Cl.
*C12N 15/62* (2006.01)
*C12N 9/50* (2006.01)

(52) U.S. Cl.
CPC . *C12N 15/62* (2013.01); *C12N 9/50* (2013.01)

(58) Field of Classification Search
CPC ........... C12N 15/1037; C12N 15/1086; C07K 2319/00
See application file for complete search history.

(56) References Cited

U.S. PATENT DOCUMENTS 5,223,408 A * 6/1993 Goeddel .............. C12N 9/6459
435/189
8,106,027 B2 1/2012 Nabel et al.

OTHER PUBLICATIONS

Wentzel et al. (001; Display of passenger proteins on the surface of *Escherichia coli* K-12 by the enterohemmorrhagic *E. coli* intimin EaeA. J. Bacteriology. 183(24): 7273-7284.*
Office Action and Search Report dated May 13, 2015 for counterpart Taiwan application No. 102139138.
English translation of the Search Report dated May 13, 2015 for counterpart Taiwan application No. 102139138.
Daniel Helman et al., Novel membrane-bound reporter molecule for sorting high producer cells by flow cytometry. Cytometry, Feb. 2014, 85(2):162-8, Epub Jun. 13, 2013.

* cited by examiner

*Primary Examiner* — Karen Cochrane Carlson
(74) *Attorney, Agent, or Firm* — WPAT, P.C., Intellectual Property Attorneys; Anthony King (57) ABSTRACT

The invention provides a method of high-throughput sorting of high expression protein-producing cell, which utilizes linking a protein and a transmembrane domain with a self-processing cleavage site and regulating the secretion of the protein or expression of protein on the cell membrane by adding self-processing cleavage enzyme inhibitor. Then, the high expression cell line can be high-throughput sorted by a detection technique. The invention also provides a recombinant nucleotide sequence and a vector used in the method and a cell sorted by the method.

14 Claims, 6 Drawing Sheets

METHOD OF HIGH-THROUGHPUT SORTING OF HIGH EXPRESSION CELL AND CELLS SORTED THEREFROM

FIELD OF THE INVENTION

The present invention relates to a recombinant nucleotide sequence and a high-throughput method for sorting high expression cells using said recombinant nucleotide sequence. Particularly, the present invention relates to a recombinant nucleotide sequence comprising self-processing cleavage enzyme site and the use thereof for high-throughput sorting high expression cells.

BACKGROUND OF THE INVENTION

High-throughput technique has become an important tool in pharmaceutical and biotechnology research. Using mammalian cells to produce recombinant protein drugs has become the mainstream in current biopharmaceutical markets. Although cell lines can provide researchers with opportunities to produce a number of particular proteins, they are not always able to do so efficiently. Some cell line clones produce a protein level lower than optimum level. Other cell line clones may produce the optimal level of an expressed protein while they fail to produce entirely functional proteins due to either the formation of incorrect structure or inappropriate post-translational modification.

Though many methods have been used for sorting high expression cell lines, a number of disadvantages exist in the prior art. For example, these include the following:

(1) Single cell line isolation: For sorting high expression cell lines which largely secrete recombinant proteins, each single cell line should be isolated and cultured in an appropriate medium. The concentration of the recombinant protein in the culture medium should then be measured individually using ELISA. This method requires a huge amount of labor and is time-consuming, so cell lines that can be measured are limited.

(2) Use of a reporter gene. High-producing cell lines can be sorted by simultaneously expressing a recombinant portent of interest and a reporter gene (such as green fluorescent protein and membrane protein CD20) and measuring the expression of a reporter gene using fluorescent activated cell sorting (FACS). However, green fluorescent protein is toxic to the living cells and CD20 is only suitable for CD20-deficient cell lines. In addition, the expression level of a reporter gene in a cell is different from that of a recombinant protein of interest, so the detection of the expression level of a reporter gene cannot show the relative productivity of said recombinant protein.

(3) Low-temperature capture. A temperature as low as 4° C. is used to allow the secreted recombinant protein to transiently anchor on a cell's surface. However, this approach is only suitable for cells which secrete antibodies.

(4) Glycosylphosphatidylinositol (GPI)-anchored fusion protein. GPI anchor is attached to the C-terminal of a recombinant protein of interest so that after post translational modification, the recombinant protein is integrated into the cell membrane and can be detected by FACS. However, phosphatidylinositol-specific phospholipase C (PI-PLC) is required for cleaving the GPI-anchor to obtain a free recombinant protein.

(5) Gel microdrop technology. Protein secretory cells are encapsulated in a gel microdrop using biotinylated argarose so that the secretory recombinant proteins are retained in said gel microdrop. The high secretory cell lines could be selected by analyzing fluorescence intensity using multiple immunofluorescence labeling techniques and FACS. However, specialized instruments are required for the preparation of a gel microdrop. Moreover, since the probability of a single cell in each microdrop is very low, further multiple antibody labeling assays are required. Thus, this approach is costly and labor-intensive.

(6) Substrate-based secretion analysis. This approach is different from gel microdrop technology. The cells are modified by biotin and cultured in a high viscosity medium to accumulate the secreted recombinant protein around periplasma. Similar to the conventional technology mentioned above, multiple antibody labeling assays are required, and thus this approach is costly and labor-intensive.

Therefore, a convenient and highly efficient method for the effective selection of high-producing cell lines is still required.

SUMMARY OF THE INVENTION

The invention provides a recombinant nucleotide sequence with a detectable label, comprising in 5' to 3' direction, a first sequence encoding a protein or a polypeptide of interest, a second sequence encoding a self-processing cleavage enzyme site and a third sequence encoding an extracellular-transmembrane domain, wherein the second sequence is located between the first sequence and the third sequence, and wherein the detectable label is located at the first sequence or the third sequence.

In one embodiment, the first sequence encoding a protein is a sequence that encodes any protein or a polypeptide of interest produced by the cells of the invention. The second sequence encoding a self-processing cleavage enzyme site of the recombinant nucleotide is a DNA sequence, which encodes a self-processing cleavage enzyme site or the sequence thereof. The third sequence encodes an extracellular-transmembrane domain which is the region that spans two layers of lipids and protein.

The invention also provides a vector comprising the recombinant nucleotide of the invention. Said vector can be any DNA or RNA molecule, such as a plasmid, a virus or other vector, which comprises the recombinant nucleotide sequence of the invention. Said vector may be inserted into the genome of a host cell or be introduced into a host cell so as to transforming the host cell. In one embodiment, the vector of the invention may comprise an additional element such as promoters and/or transcription regulatory elements.

The invention further provides a method of high-throughput sorting of protein-expression cells, comprising the following steps:

(a) constructing a vector comprising a recombinant nucleotide sequence with a detectable label, which comprises, in 5' to 3' direction, a first sequence encoding a protein or a polypeptide of interest, a second sequence encoding a self-processing cleavage site and a third sequence encoding an extracellular-transmembrane domain, wherein the second sequence is located between the first sequence and the third sequence, and wherein the detectable label is located at the first sequence or the third sequence;

(b) transfecting a cell with the vector of (a);

(c) adding a self-processing cleavage enzyme inhibitor so that the recombinant protein encoded by the recombinant sequence of the vector of (a) can be transiently anchored on a cell surface; and (d) determining the detectable label to sort the recombinant protein expressing cells that express anchored recombinant protein on the cell surface to obtain protein-expression cells.

DETAILED DESCRIPTION OF THE INVENTION

Production of recombinant proteins using a mammalian cell expression system is becoming increasingly important because of its post transitional modification and glycosylation to stabilize the structure and function of recombinant proteins and ensure the quality and utility of said recombinant protein products. However, the cost of mammalian cell culture is very high, and it is necessary to use a single cell line that highly produces the recombinant protein of interest. Therefore, the present invention develops a platform that is easy to operate and can be coupled with FACS for the efficient high-throughput selection of high-producing cell lines. In particular, the cell lines sorted by the method of the invention can directly secrete a large number of recombinant proteins of interest without and the need for subsequent treatment. Accordingly, the amount of recombinant protein produced can be optimized to satisfy market demand.

In one aspect, the invention provides a recombinant nucleotide sequence with a detectable label, comprising in 5' to 3' direction, a first sequence encoding a protein or a polypeptide of interest, a second sequence encoding a self-processing cleavage enzyme site and a third sequence encoding an extracellular-transmembrane domain, wherein the second sequence is located between the first sequence and the third sequence, and wherein the detectable label is located at the first sequence or the third sequence.

In one embodiment, the first, the second and the third sequences of the recombinant nucleotide sequence are in 5' to 3' direction, wherein the second sequence is located between the first sequence and the third sequence.

The first sequence encoding a protein is a sequence that encodes any protein or a polypeptide of interest produced by the cells of the invention. Examples of a protein or a polypeptide of interest include, but are not limited to, antibody cDNA libraries, antibodies, antigens, immuno-modulating proteins, antibiotics, protein vaccines, growth factors, cytokines and so on.

The "self-processing cleavage site" is a post-translational or co-translational processing cleavage site. The second sequence encoding a self-processing cleavage enzyme site of the recombinant nucleotide is a DNA sequence, which encodes a self-processing cleavage enzyme site or the sequence thereof. Once transcribed, said sequence may regulate rapid intercellular cleavage of the protein or polypeptide comprising said self-processing cleavage enzyme site, so as to produce discontinuous mature proteins or polypeptides. Endoproteases in eukaryotes have a self-processing cleavage site and therefore can be used in the invention. Specifically, any proteases in the trans-Golgi network and the corresponding cleavage fragments can be used as the self-processing cleavage site of the invention. Preferably, examples of a self-processing cleavage site include, but are not limited to, Furin consensus sequence RXK(R)R (SEQ ID NO:1), Furin cleavage sequence RAKR (SEQ ID NO:2), Xa factor cleavage sequence or IE(D)GR (SEQ ID NO:3), peptide I cleavage sequence or LAGFATVAQA (SEQ ID NO:4), thrombin enzyme cleavage sequence or LVPRGS (SEQ ID NO:5), and PC1/3, PC2, PACE4 and PC5 of proprotein convertase family in the trans-Golgi network. More preferably, said self-processing cleavage site is Furin consensus sequence RXK(R)R or Furin cleavage sequence RAKR. Said Furin cleavage site has the consensus sequence of PXK(R)R. Said Furin cleavage site can be cleaved by *Bacillus* subtilisin-like proteases, such as furin or other serine proteases.

The third sequence encodes an extracellular-transmembrane domain which is the region that spans two layers of lipids and protein. Any extracellular-transmembrane domain can be used for the invention.

The recombinant nucleotide sequence of the invention bears a detectable label. Said detectable label may be a fluorescent label, a radiolabel or an antigen label. Preferably, said detectable is a fluorescent label.

The recombinant nucleotide sequence of the invention can be constructed based on known techniques of molecular biology, for example, Sambrook et al., Molecular Cloning: A Laboratory Manual ($2^{nd}$ edition, Coldspring Harbor Laboratory Press, Plainview, N.Y. (1989)).

In one aspect, the invention provides a vector comprising the recombinant nucleotide of the invention. Said vector can be any DNA or RNA molecule, such as a plasmid, a virus or other vector, which comprises the recombinant nucleotide sequence of the invention. Said vector may be inserted into the genome of a host cell or be introduced into a host cell so as to transform the host cell. The vector of the invention may comprise an additional element such as promoters and/or transcription regulatory elements. Any vector that is effective for introduction of nucleic acids into cells and results in protein/polypeptide expression can be employed for the invention.

In one aspect, the invention provides a method of high-throughput sorting of protein-expression cells, comprising the following steps:
(a) constructing a vector comprising a recombinant nucleotide sequence with a detectable label, which comprises, in 5' to 3' direction, a first sequence encoding a protein or a polypeptide of interest, a second sequence encoding a self-processing cleavage site and a third sequence encoding an extracellular-transmembrane domain, wherein the second sequence is located between the first sequence and the third sequence, and wherein the detectable label is located at the first sequence or the third sequence;
(b) transfecting a cell with the vector of (a);
(c) adding a self-processing cleavage enzyme inhibitor so that the recombinant protein encoded by the recombinant sequence of the vector of (a) can be transiently anchored on the cell surface; and
(d) determining the detectable label to sort the recombinant protein expressing cells that express anchored recombinant protein on the cell surface to obtain protein-expression cells.

The invention utilizes a self-processing cleavage site, for example, the cleavage fragment (RAKR) of furin protease, to link a protein and a transmembrane protein sequence. By adding self-processing cleavage enzyme inhibitors, the secretion of the recombinant protein or expression of protein on the cell membrane may be regulated. The cell lines with high productivity, high-affinity antigen-specific or superior characteristics can then be high-throughput sorted by a detection technique (e.g., flow cytometry).

According to the invention, the vector mentioned above may be introduced into eukaryote cells by transfection. Any cells suitable for producing the protein or polypeptide of interest can be used for the invention. Examples of eukaryote cells include, but are not limited to, insect cells, animal cells, plant cells, and yeast.

Then, the recombinant protein encoded by the recombinant sequence of the vector can be transiently anchored on a cell surface with the addition of a self-processing cleavage enzyme inhibitor. For example, since the Furin protease activity is inhibited by the addition of Furin inhibitor (Dec-RVKR-CMK); the recombinant sequence of the invention will not be cleaved by the Furin protease and is stably expressed on the surface of the cell membrane. Any suitable detection technique for determining a detectable label can be used for the sorting of the cell lines anchored on the cell surface, and thus the protein-producing cell lines can be obtained. Preferably, flow cytometry is used for detection.

In one aspect, the invention provides a protein-producing cell that is obtained from the method of the invention.

The vectors and the method of the invention can be applied to various uses as follows:
(1) Screening of high expression recombinant protein-secreting cell lines: after introducing transgenes into mammalian cells, the secretion of recombinant proteins is highly specific. The invention enables recombinant proteins to transiently anchor on the surface of the cell membrane with the use of self-processing cleavage enzyme inhibitors, preferably combined with FACS, so as to screen high protein-producing cell lines. After the inhibitors are removed, the cell lines can continuously secrete the recombinant proteins with a high yield. This significantly reduces the cost for high protein-producing cell line screening, and increases the production of recombinant proteins for clinical needs.
(2) Screening of high expression recombinant protein-producing cell lines in lysosome: some recombinant proteins (such as perforin, granzymes and so on) are stored in lysosome of mammalian cells. It is not easy to screen the cell lines with high level expression. The invention enables a small amount of recombinant proteins to transiently anchor on the surface of the cell membrane with the use of self-processing cleavage enzyme inhibitors, preferably combined with FACS, so as to screen high expression protein-producing cell lines. After the inhibitors are removed, a large amount of recombinant proteins will accumulat in lysosome of the cell lines, thereby allowing a significant amount of time to be saved.

(3) Rapid screening antigen-specific antibody: couple an antibody cDNA library with the system of the invention and then transfect into mammalian cells. The invention enables the antibody to transiently anchor on the cell membrane with the use of self-processing cleavage enzyme inhibitors so as to rapidly screen the cell lines which express antigen-specific antibodies using flow cytometry accompanied with a specific antigen probe. After the inhibitor is removed, said cell lines can continuously secrete antigen-specific antibodies for function and affinity analysis without further cloning technology. This invention shortens the time needed to generate highly antigen-specific antibodies.

(4) Improving affinity of an antigen-specific antibody: couple a random mutant specific antibody library with the system of the invention and then transfect into mammalian cells for expression. The invention enables the antibody to transiently anchor on the cell membrane with the use of self-processing cleavage enzyme inhibitor so as to rapidly screen the cell lines producing antibodies with a high affinity for the antigen using flow cytometry accompanied with specific antigen probe and specific conditions. After the inhibitor is removed, secreted antibodies are obtained for function and affinity analysis without further cloning technology. This invention shortens the time needed to develop antibody drugs with high affinity.

(5) Improving or changing the function of recombinant proteins: couple a random mutant recombinant protein library with the system of the invention and then transfect the recombinant protein into mammalian cells for expression. The invention enables the recombinant protein to transiently anchor on the cell membrane with the use of self-processing cleavage enzyme inhibitors, preferably using flow cytometry accompanied with specific substrates (such as protease-specific substrate) and specific conditions (such as pH condition) so as to rapidly screen the recombinant protein-producing cell lines with superior characteristics (such as high protease activity, anti-acid or anti-alkali performance). After the inhibitor is removed, secreted recombinant proteins are obtained for function analysis without further cloning technology. This invention shortens the time needed to develop recombinant proteins with superior characteristics.

EXAMPLE

Example 1

Selection of High-Producing Recombinant Protein Cell Lines

Figure 1:
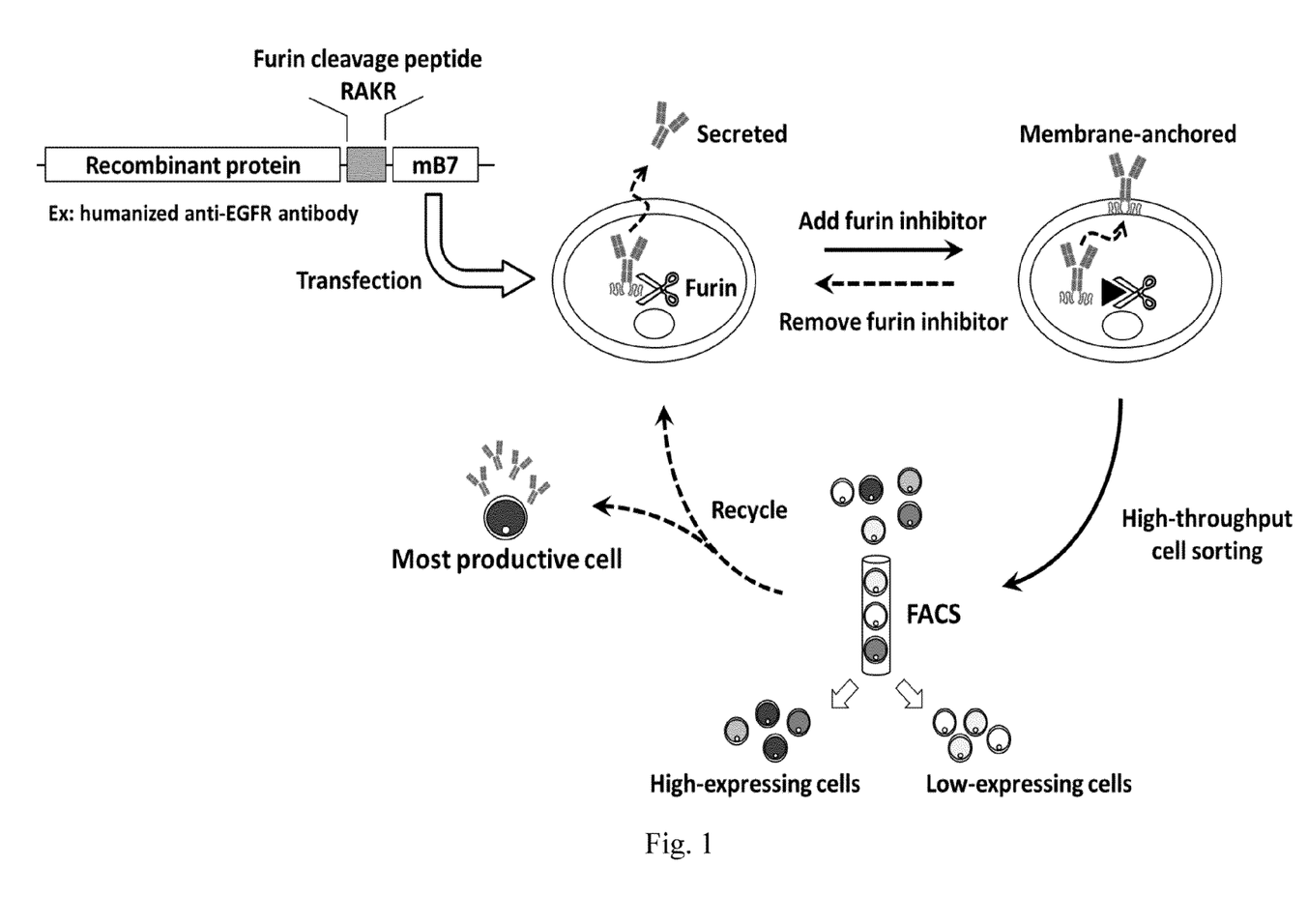
FIG. 1 shows a highly secreting recombinant protein cell line which was screened by the transient membrane protein expression system of the invention. A furin cleavage peptide (RAKR) was used to join a recombinant protein and the extracellular-transmembrane domains of the mouse B7 gene sequence (mB7) with the use of cloning technology. Said gene is transfected into mammalian cells. The recombinant protein-RAKR-mB7 can be stably expressed on a cell surface by using the furin inhibitor to block furin activity, allowing high-throughput selection of the cells which highly express recombinant protein-RAKR-mB7 on the cell surface with the use of flow cytometry. Once the furin inhibitor is removed (furin activity recovered), the cell can continuously secrete the recombinant protein for large-scale production of recombinant proteins.

To construct anti-EGFR Ab-RAKR-mB7 as shown in FIG. 1, a furin cleavage peptide (RAKR) was used to join an anti-EGFR antibody (a secretory humanized antibody) and the extracellular-transmembrane domains of the mouse B7 gene sequence (mB7) using cloning technology. The gene was transfected into mammalian cells (human embryonic kidney cells, HEK-293). Under normal conditions, rich furin protease in Golgi can effectively cleave a furin cleavage site (PAKR) between anti-EGFR antibody and mB7 to allow secretion of the anti-EGFR antibody into an extracellular matrix. When furin inhibitor (DEC-RVKR-CMK) was added, to inhibit the activity of the furin protease, the anti-EGFR Ab-RAKR-mB7 would not be cleaved by furin protease and would be stably anchored on the cell membrane surface. Then, FITC-conjugated anti-human antibody was used to label the anti-EGFR Ab-RAKR-mB7 on the cell membranes. By using FACS, the cells with high expression of anti-EGFR Ab-RAKR-mB7 on their cell membranes can be rapidly and high-throughput sorted. Once the furin inhibitor (DEC-RVKR-CMK) were removed, said clones are high-producing cell lines which largely secrete anti-EGFR antibodies (see FIG. 1).

Figure 2:
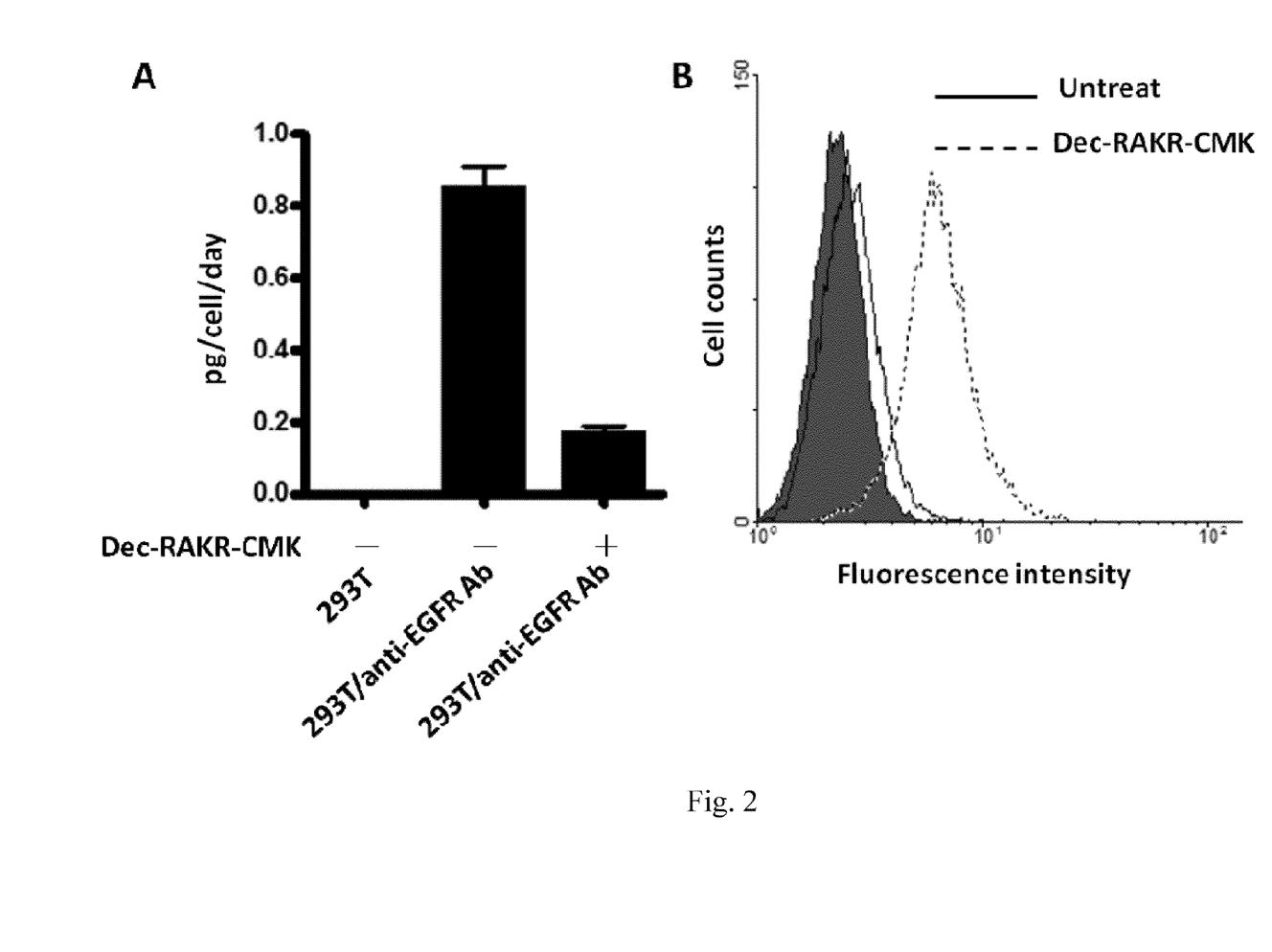
FIG. 2 shows the regulation of the cells which secrete anti-EGFR antibody or express anti-EGFR Ab-RAKR-mB7 on membrane with the use of furin inhibitor. (A) To detect the concentration of anti-EGFR antibody of 293T/anti-EGFR cell culture, Dec-RVKR-CMK was used as furin inhibitor. The Y axis represents concentration of the secreted anti-EGFR antibody, while the X axis represents cell groups. The results indicate that 293T/anti-EGFR can stably secrete anti-EGFR antibody; however, after the addition of furin inhibitor, the secretion of anti-EGFR antibody decreased. (B) To detect anti-EGFR Ab-RAKR-mB7 expression of 293T/anti-EGFR on cell membrane, FACS technology combined with FITC conjugated anti-human IgG antibody was used. The filled region represents 293T cells as control group; the solid line represents 293T/anti-EGFR cell without furin inhibitor; the dashed line represents 293T/anti-EGFR cell with furin inhibitor. The results indicate that the inhibition of furin activity makes anti-EGFR antibody change to anti-EGFR Ab-RAKR-mB7, so as to express on the cell membrane stably.

To Transfer a Secretory Recombinant Protein to Membrane Expression Recombinant Protein by Inhibiting Furin Protease Activity Take a humanized anti-EGFR antibody, for example; we transfected an anti-EGFR Ab-RAKR-mB7 gene into a human embryonic kidney cell with a Lentivirus vector to construct a 293T/anti-EGFR cell line. In the absence of a furin inhibitor (Dec-RVKR-CMK), said 293T/anti-EGFR can continuously secrete anti-EGFR antibody into extracellular matrix (see FIG. 2A). In contrast, when furin inhibitor was added to inhibit furin protease activity, decreased secretion of anti-EGFR antibody occurred in 293T/anti-EGFR cells (FIG. 2A) and the expression of anti-EGFR Ab-RAKR-mB7 was on the cell membrane (FIG. 2B).

Figure 3:
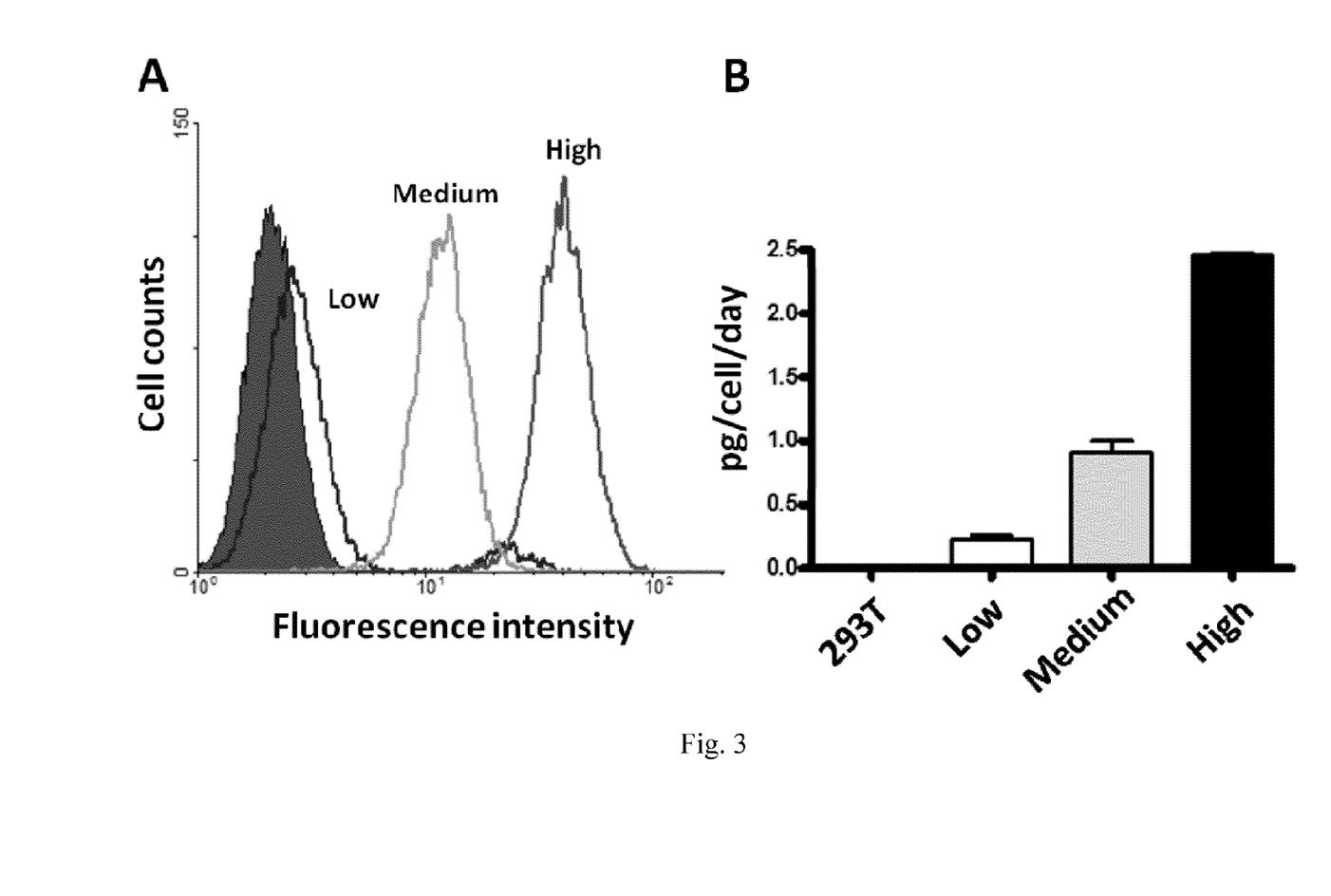
FIG. 3 shows the correlation of anti-EGFR Ab-RAKR-mB7 expression on cell membrane and anti-EGFR antibody secretion. (A) The Y axis represents cell counts, and the X axis represents fluorescence intensity. The Red part represents 293T as control group. With the use of FACS technology combined with FITC conjugated anti-human IgG antibody, the 293T/anti-EGFR cells respectively with low (blue line), medium (orange line) and high (green line) expression of anti-EGFR Ab-RAKRmB7 are sorted. (B) The Y axis represents the concentration of anti-EGFR antibody. The X axis represents cell groups. From left to right, they are respectively 293T cell, 293T/anti-EGFR cell with low anti-EGFR Ab-RAKR-mB7 expression, 293T/anti-EGFR cell with medium anti-EGFR Ab-RAKR-mB7 expression, and 293T/anti-EGFR cell with high anti-EGFR Ab-RAKR-mB7 expression.

Use of FACS for the Selection of Recombinant Protein-Secreting Cells with Different Productivity, as Furin Protease Activity is Inhibited Said 293T/anti-EGFR cells constructed by the Lentivirus vector mentioned above exhibit highly variable productivity characteristics in anti-EGFR antibody secretion. To confirm whether the transient membrane protein expression system of the invention accompanied with FACS technology is useful for the selection of cell lines with superior productivity, after the addition of a furin inhibitor, we used FACS for the selection of cell lines with high, medium and low expression on the membrane. The cells were cultivated and amplified (FIG. 3A). After removal of the furin inhibitor, the amount of anti-EGFR antibody secretion was determined for each group. The results indicate that, after the addition of the furin inhibitor, the cell lines with high expression anti-EGFR Ab-RAKR-mB7 on the cell membrane selected by the use of FACS were those cell lines which can highly secrete an anti-EGFR antibody when the furin inhibitor was removed (FIG. 3B).

Figure 4:
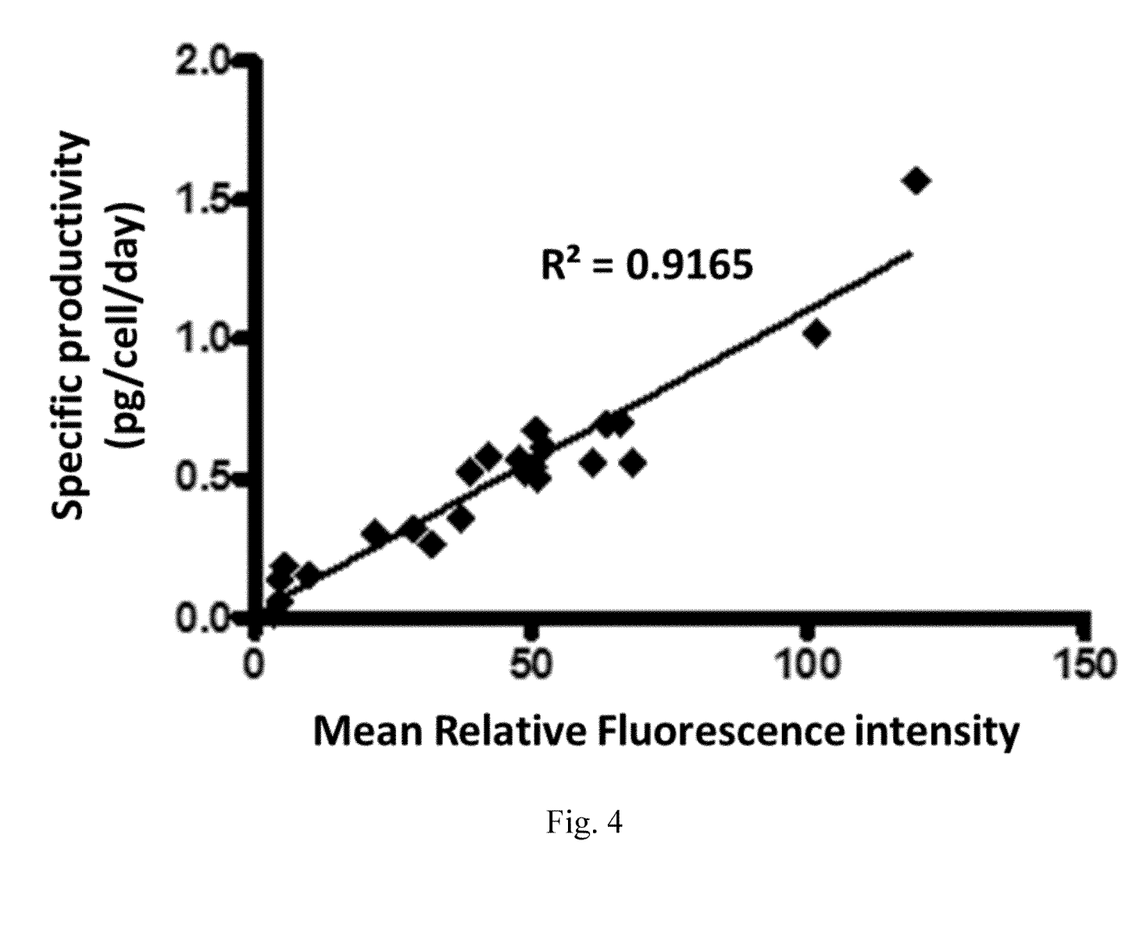
FIG. 4 shows the correlation of anti-EGFR Ab-RAKR-mB7 expression on cell membrane and the production of anti-EGFR antibody secretion. The X axis represents the expression of anti-EGFR Ab-RAKR-mB7 on cell membrane (mean relative fluorescence intensity). The Y axis represents the production of anti-EGFR antibody secreted by cells. Each dot represents a single individual 293T/anti-EGFR cell. The results indicate that the expression of anti-EGFR Ab-RAKR-mB7 is highly correlated with the production of anti-EGFR antibody ($R^2$=0.9165).

Surface Expression Level of Recombinant Protein is Highly Correlated with Cell Secretion Level In order to accurately evaluate the productivity of each cell in recombinant protein secretion, we used single cell line separation to obtain 23 293T/anti-EGFR single cells. The cells were cultivated and amplified. After the addition of the furin inhibitor, the expression level of anti-EGFR Ab-RAKR-mB7 on the cell membrane was measured by FACS and the expression level was converted as an average of fluorescence intensity. After the removal of the furin inhibitor, the anti-EGFR antibody concentration of each cell line was determined using ELISA. The results indicate that the level of secreted recombinant protein in cells is highly correlated with the surface-expression level of anchored recombinant protein-RAKR-mB7 in furin inhibitor-treated cells ($R^2=0.9165$) (see FIG. 4). Thus, the method of the present invention accompanied with FACS technology is useful for the selection of high producing recombinant protein cells in a rapid and accurate manner.

Example 2

Selection of High-Producing Recombinant Protein Cell Lines in Lysosomes

Figure 5:
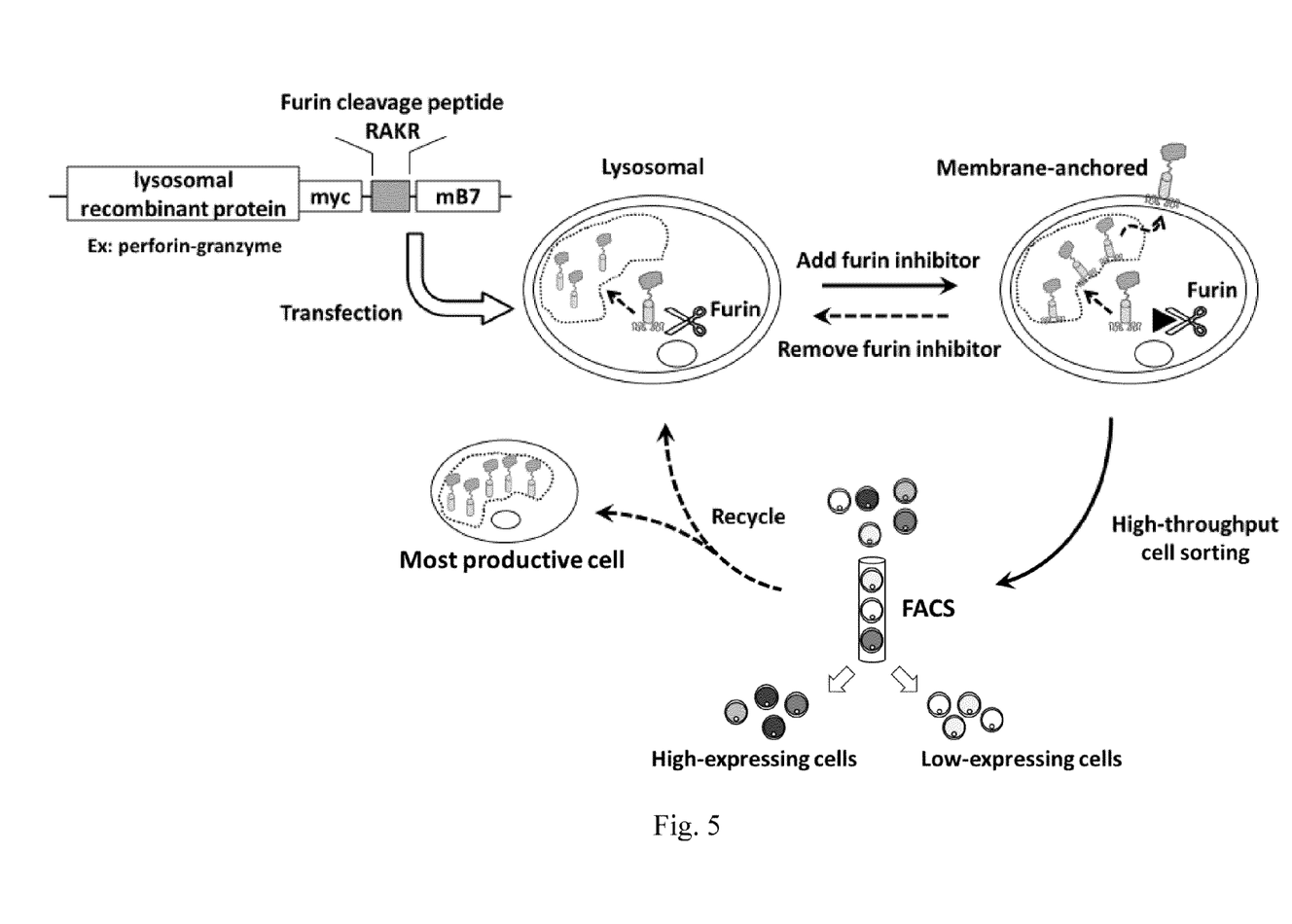
FIG. 5 shows a cell line screened by a transient membrane protein expression system which highly expresses recombinant protein in lysosome. A furin cleavage peptide (RAKR) was used to join C-terminal of recombinant protein and the extracellular-transmembrane domains of the mouse B7 gene sequence (mB7) using cloning technology. The gene was transfected into mammalian cells. When furin inhibitor was added to inhibit the activity of the furin protease, recombinant protein-PAKR-mB7 would be stably anchored on the surface of lysosome. If excess recombinant proteins were stored in lysosomes, part of the recombinant proteins would be excluded through secretion or exocytosis. Then, the recombinant protein-RAKR-mB7 would be anchored on cell membrane, and thus a high expression cell line can be high-throughput sorted using flow cytometry technology. Once the furin inhibitor was removed, said cell lines are those which highly store recombinant proteins in lysosomes, and thus the cell line is useful for large scale production of recombinant proteins expressed in lysosomes in a large scale.

Example 2 exemplifies a perforin-granzyme fusion protein (PCD-GB) which is expressed in lysosome. To construct PCD-GB-RAKR-mB7 as shown in FIG. 5, a furin cleavage peptide (RAKR) was used to join PCD-GB and mB7 using cloning technology. The gene was transfected into mammalian cells (Chinese Hamster Ovary cells, LEC1). Under normal conditions, rich furin protease in Golgi can effectively cleave furin cleavage site (PAKR) between PCD-GB and mB7 so that PCD-GB would be stored in lysosome. When furin inhibitor (DEC-RVKR-CMK) was added to inhibit the activity of the furin protease, PCD-GB-PAKR-mB7 would not be cleaved by the furin protease and would be stably anchored on the surface of lysosome. If excess proteins were stored in lysosomes, part of PCD-GB-RAKR-mB7 would be anchored on the cell membrane due to secretion or exocytosis. Then, an FITC-conjugated antibody was used to label the PCD-GB-RAKR-mB7 on the cell membranes. By using FACS, the cells with high expression of anti-EGFR Ab-RAKR-mB7 on their cell membranes can be rapidly and high-throughput sorted. Once the furin inhibitor (DEC-RVKR-CMK) was removed, said clones were high-producing cell lines which highly express PCD-GB in lysosomes (see FIG. 5).

Figure 6:
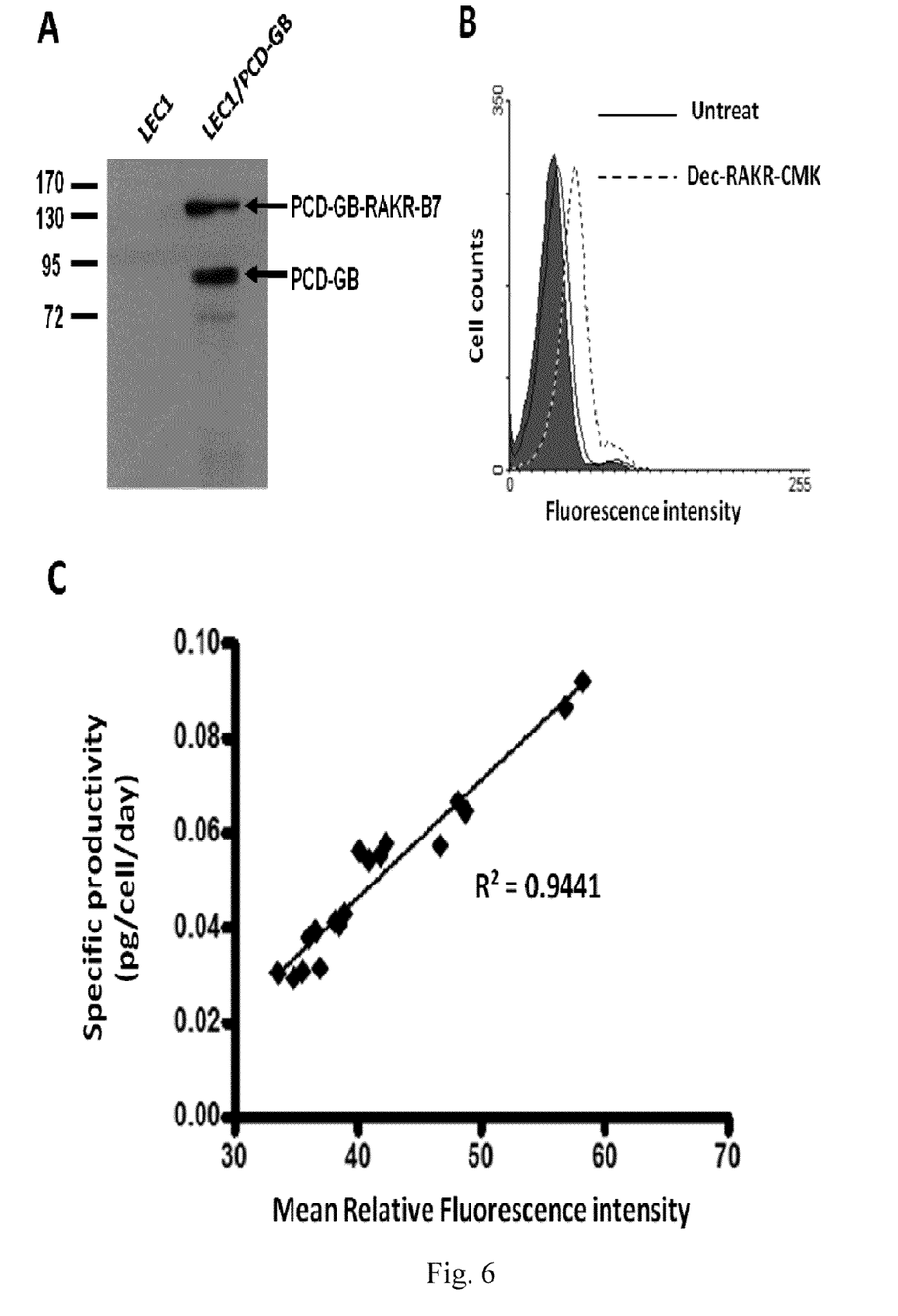
FIG. 6 shows the regulation of the cells which store PCD-GB in lysosomes or the expression of PCD-GB-RAKR-mB7 on membrane with the use of furin inhibitor. (A) To detect the expression of PCD-GB recombinant protein in LEC1 and LEC1/PCD-GB cells, Western blot technique accompanied with mouse anti-myc antibody and goat anti-mouse IgG-HRP was used. (B) Furin inhibitor (Dec-RVKR-CMK) was used to inhibit the furin activity of LEC1 and LEC1/PCD-GB cells. Then, to detect the expression of PCD-GB-RAKR-mB7 on cell membrane, FACS technology accompanied with mouse anti-myc antibody and goat anti-mouse IgG-HRP was used. The filled region represents LEC1 cells as control group; solid line represents LEC1/PCD-GB cells without furin inhibitor; dashed line represents LEC1/PCD-GB cells with furin inhibitor. (C) The X axis represents the expression of PCD-GB-RAKR-mB7 on cell membrane (mean relative fluorescence intensity). The Y axis represents the production of PCD-GB stored in lysosomes. Each dot represents a single individual LEC1/PCD-GB cell. The results indicate that the expression of PCD-GB-RAKR-mB7 on cell membrane is highly correlated with the production of PCD-GB stored in lysosomes ($R^2$=0.9441).

We transfected a PCD-GB-RAKR-mB7 gene into LEC1 cells with Lentivirus vector to construct an LEC1/PCD-GB cell line. In the absence of furin inhibitor (Dec-RVKR-CMK), the furin protease would lyse said PCD-GB-RAKR-mB7 into PCD-GB and store PCD-GB in lysosomes (FIG. 6A). As shown in FIG. 6A, some non-lysed PCD-GB-RAKR-mB7 are immature PCD-GB-RAKR-mB7 proteins and have not yet transported into the trans-Golgi network. In contrast, when the furin inhibitor was added to inhibit furin protease activity, few PCD-GB-RAKR-mB7 would be detected on the LEC1/PCD-GB cell membrane using FACS technology accompanied with anti-myc antibody (which is a tag located on the C-terminal of PCD-GB) (see FIG. 6B).

In order to accurately evaluate the storage of recombinant protein of each cell, we used single cell line separation to obtain 18 LEC1/PCD-GB single cells. They were cultivated and amplified. After the addition of the furin inhibitor, the expression level of PCD-GB-RAKR-mB7 on the cell membrane was measured by FACS and the expression level was converted as an average of fluorescence intensity. After the removal of the furin inhibitor, the PCD-GB concentration in lysosomes of each cell line was determined using ELISA. The results indicate that the PCD-GB-RAKR-mB7 expression level on the cell membrane is highly correlated with PCD-GB storage in lysosomes in said cell ($R^2=0.9441$) (see FIG. 6C). Thus, the method of the present invention accompanied with FACS technology is useful, in a rapid and accurate manner, for selection of cell lines which highly express recombinant proteins in lysosomes.

What is claimed is:

1. A method of high-throughput sorting of protein-expression cells, comprising the following steps:
   (a) constructing a vector comprising a recombinant nucleotide sequence with a detectable label, which comprises, in 5' to 3' direction, a first sequence encoding a protein or a polypeptide of interest, a second sequence encoding a self-processing cleavage site and a third sequence encoding an extracellular-transmembrane domain, wherein the second sequence is located between the first sequence and the third sequence, and wherein the detectable label is located at the first sequence or the third sequence;
   (b) transfecting a cell with the vector of (a);
   (c) adding a self-processing cleavage enzyme inhibitor so that the recombinant protein encoded by the recombinant sequence of the vector of (a) can be transiently anchored on a cell surface; and
   (d) determining the detectable label to sort the recombinant protein expressing cells that express anchored recombinant protein on the cell surface to obtain protein-expression cells.

2. The method of claim 1, wherein the second sequence encoding a self-processing cleavage enzyme site is the self-processing cleavage site of endoproteases in eukaryotes.

3. The method of claim 1, wherein the second sequence encoding a self-processing cleavage enzyme site is Furin consensus sequence RXK(R)R, Furin cleavage sequence RAKR, Xa factor cleavage sequence or IE(D)GR, peptide I cleavage sequence or LAGFATVAQA, thrombin enzyme cleavage sequence or LVPRGS, or PC1/3, PC2, PACE4 and PC5 of proprotein convertase family in the trans-Golgi network.

4. The method of claim 1, wherein the second sequence encoding a self-processing cleavage enzyme site is Furin consensus sequence RXK(R)R or Furin cleavage sequence RAKR.

5. The method of claim 1, wherein the protein or polypeptide is an antibody, an antigen, an immuno-modulating protein, an antibiotic, a protein vaccine, a growth factor, or a cytokine.

6. The method of claim 1, wherein the detectable label may be a fluorescent label, a radiolabel or an antigen label.

7. The method of claim 1, wherein the detectable label may be a fluorescent label.

8. The method of claim 1, which is useful for high-throughput sorting of protein-producing cells.

9. The method of claim 1, which is useful for sorting of cells that highly secrete recombinant proteins.

10. The method of claim 1, which is useful for sorting of cells that highly express recombinant proteins in lysosomes.

11. The method of claim 1, which is useful for sorting of cells expressing antigen-specific antibody.

12. The method of claim 1, which is useful for sorting of cells expressing antigen-specific antibody with improved affinity.

13. The method of claim 1, which is useful for sorting of cells expressing recombinant proteins with improved or changed function.

14. The method of claim 1, wherein the first sequence encodes an antibody cDNA library, an antibody, an antigen, an immuno-modulating protein, an antibiotic, a protein vaccine, a growth factor or a cytokine.

* * * * *

```
SEQUENCE LISTING

<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: Furin consensus sequence
<220> FEATURE:
<221> NAME/KEY: MUTAGEN
<222> LOCATION: (1)..(5)
<223> OTHER INFORMATION: appropriate amino acid

<400> SEQUENCE: 1

Arg Xaa Lys Arg Arg
1               5

<210> SEQ ID NO 2
<211> LENGTH: 4
<212> TYPE: PRT
<213> ORGANISM: Artificial Sequence
<220> FEATURE:
<223> OTHER INFORMATION: Furin cleavage sequence
<220> FEATURE:
<221> NAME/KEY: MUTAGEN
<222> LOCATION: (1)..(4)

<400> SEQUENCE: 2

Arg Ala Lys Arg
1

<210> SEQ ID NO 3
<211> LENGTH: 5
<212> TYPE: PRT
<213> ORGANISM: Artificial Sequence
<220> FEATURE:
<223> OTHER INFORMATION: Xa factor cleavage sequence
```

```
<220> FEATURE:
<221> NAME/KEY: MUTAGEN
<222> LOCATION: (1)..(5)

<400> SEQUENCE: 3

Ile Glu Asp Gly Arg
1               5

<210> SEQ ID NO 4
<211> LENGTH: 10
<212> TYPE: PRT
<213> ORGANISM: Artificial Sequence
<220> FEATURE:
<223> OTHER INFORMATION: Peptide I cleavage sequence
<220> FEATURE:
<221> NAME/KEY: MUTAGEN
<222> LOCATION: (1)..(10)

<400> SEQUENCE: 4

Leu Ala Gly Phe Ala Thr Val Ala Gln Ala
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Thrombin enzyme cleavage sequence
<220> FEATURE:
<221> NAME/KEY: MUTAGEN
<222> LOCATION: (1)..(6)

<400> SEQUENCE: 5

Leu Val Pro Arg Gly Ser
1               5
```